United States Patent [19] [11] 3,931,189
Langbein et al. [45] Jan. 6, 1976

[54] N-(HETEROARYL-METHYL)-6,14-(ENDOETHANO OR ENDOETHENO)-7α-HYDROXYALKYL-TETRAHYDRO-NORORIPAVINES OR-NORTHEBAINES AND SALTS THEREOF

[75] Inventors: Adolf Langbein; Herbert Merz; Gerhard Walther; Kalus Stockhaus, all of Ingelheim am Rhein, Germany

[73] Assignee: Boehringer Ingelheim GmbH, Ingelheim am Rhein, Germany

[22] Filed: June 13, 1973

[21] Appl. No.: 369,500

[30] Foreign Application Priority Data
June 21, 1972 Germany............................ 2230154

[52] U.S. Cl................................. 260/285; 424/260
[51] Int. Cl.²....................................... C07D 489/12
[58] Field of Search.................................... 260/285

[56] References Cited
UNITED STATES PATENTS
3,285,914 11/1966 Gordon............................ 260/285
3,442,900 5/1969 Bentley et al..................... 260/285
3,793,329 2/1974 Merz et al........................ 260/285
FOREIGN PATENTS OR APPLICATIONS
1,223,445 2/1971 United Kingdom................ 260/285

Primary Examiner—Raymond V. Rush
Assistant Examiner—Mary C. Vaughn
Attorney, Agent, or Firm—Hammond & Littell

[57] ABSTRACT
Compounds of the formula

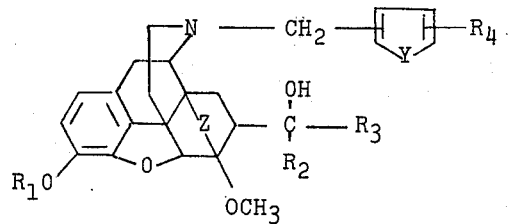

wherein
$R_1$ is hydrogen, methyl or acetyl,
$R_2$ is hydrogen or methyl,
$R_3$ is hydrogen, methyl, n-propyl, phenethyl or phenyl,
$R_4$ is hydrogen or methyl,
Z is —CH=CH— or —CH$_2$—CH$_2$—, and
Y is oxygen or sulfur,
and non-toxic, pharmacologically acceptable acid addition salts thereof; the compounds as well as their salts are useful as analgesics and antitussives.

6 Claims, No Drawings

N-(HETEROARYL-METHYL)-6,14-(ENDOETHANO OR ENDOETHENO)-7α-HYDROXYALKYL-TETRAHYDRO-NORORIPAVINES OR -NORTHEBAINES AND SALTS THEREOF

This invention relates to a novel N-(heteroarylmethyl)-7α-hydroxyalkyl-6,14-(endoetheno or endoethano)-tetrahydro-nororipavines or -northebaines and non-toxic acid addition salts thereof, as well as to various methods of preparing these compounds.

THE PRIOR ART

In J.A.C.S. 89, 3267 et seq. (1967), it is disclosed that compounds of the formula

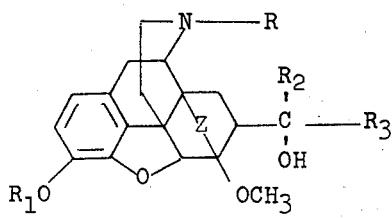

wherein
R is allyl or cyclopropylmethyl,
$R_1$ is hydrogen or methyl,
$R_2$ and $R_3$ are hydrogen, alkyl, phenyl or aralkyl, and
Z is —CH=CH— or —$CH_2$—$CH_2$—,
are very strong central analgesics and, in addition, exhibit morphine-antagonistic properties.

THE INVENTION

More particularly, the present invention relates to a novel class of N-(furylmethyl or thienylmethyl)-7α-hydroxy-alkyl-6,14-(endoethano or endoetheno)-tetrahydro-norori-pavines or -northebaines represented by the formula

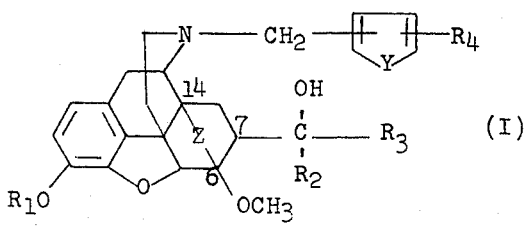

wherein
$R_1$ is hydrogen, methyl or acetyl,
$R_2$ is hydrogen or methyl,
$R_3$ is hydrogen, methyl, n-propyl, phenethyl or phenyl,
$R_4$ is hydrogen or methyl,
Z is —CH=CH— or —$CH_2$—$CH_2$—, and
Y is oxygen or sulfur, and non-toxic, pharmacologically acceptable acid addition salts thereof.

A preferred subgenus thereunder is constituted by those compounds of the formula I wherein $R_1$ is hydrogen, Y is oxygen, and the remaining variables have the meanings previously defined.

The compounds may form isomers in the 7-position; "7α" means that the hydroxyalkyl substituent lies below the plane of the paper.

The compounds embraced by formula I may be prepared by the following methods.

Method A

By reacting an oripavine or thebaine derivative of the formula

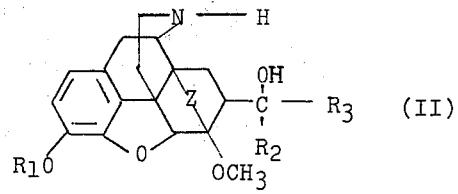

wherein $R_1$, $R_2$, $R_3$ and Z have the same meanings as in formula I, with a heteroarylmethyl derivative of the formula

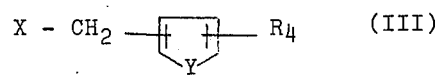

wherein
$R_4$ and Y have the meanings previously defined, and
X is halogen, preferably chlorine, bromine or iodine, alkyl—$SO_2$—O—, aryl —$SO_2$—O— or trialkyl—ammonium, preferably $(CH_3)_3$—N—.

The reaction of the compound of the formula II is performed with the calculated amount, or a slight excess thereof, of the heteroarylmethyl derivative of the formula III, optionally in the presence of an acid-binding agent. Examples of suitable acid-binding agents are tertiary amines, such as triethylamine or N,N-dicyclohexyl-ethylamine; alkali metal carbonates, such as sodium carbonate or potassium carbonate; alkali metal bicarbonates, preferably sodium bicarbonate; or alkali metal hydroxides or oxides. The reaction is advantageously carried out in an inert organic solvent medium, such as tetrahydrofuran, dioxane, methylene chloride, dimethylformamide, dimethylsulfoxide or a mixture of two or more of these, preferably mixtures of tetrahydrofuran and dimethylformamide. The reaction temperature may vary within wide limits, but a temperature between 0°C. and the boiling point of the particular solvent medium which is used is preferred. After completion of the reaction, the reaction product is isolated and crystallized by conventional methods.

Method B

By reacting a compound of the formula II with formaldehyde and a furan or thiophene of the formula

wherein Y and $R_4$ have the meanings defined above.

The reaction is carried out in weakly acid solution, especially in an acetic acid solution, and preferably in aqueous 50% acetic acid. Other suitable solvents are water, lower alkanols, tetrahydrofuran, dioxane or mixtures of any two or more of these. The furan or thiophene of the formula IV is provided in the stoichiometric amount or in slight excess thereover, either dissolved or suspended in the solvent medium. The formaldehyde may be provided in the form of paraformaldehyde or preferably in the form of an aqueous solution in the calculated amount or in excess thereover. The reaction temperature may vary between −10°C. and the boiling point of the particular solvent medium which is employed, but the preferred temperature is 25°C. After completion of the reaction, the reaction product is isolated and crystallized by conventional methods.

Method C

By reducing a compound of the formula

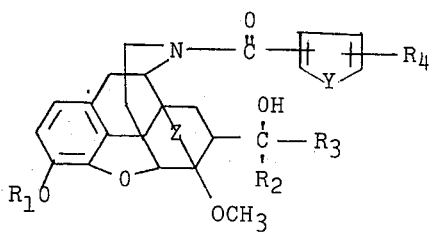 (V)

wherein $R_1$, $R_2$, $R_3$, $R_4$, Z and Y have the meanings previously defined, or, for the preparation of a compound of the formula I wherein $R_2$ is hydrogen, by reducing a compound of the formula

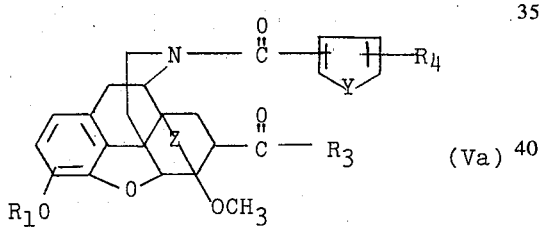 (Va)

wherein $R_1$, $R_3$, $R_4$, Z and Y have the meanings previously defined.

Among the various suitable reduction methods, the reduction with a complex hydride, in particular with lithium aluminum hydride, is preferably used. Either the calculated quantity or, preferably, an excess of the hydride, advantageously up to double the calculated quantity, is provided. The reduction is advantageously performed in a suitable inert solvent or solvent mixture, such as ethers, but preferably in tetrahydrofuran. The reaction temperature is variable within wide limits. Temperatures between 0°C. and the boiling point of the solvent or mixture of solvents are preferred.

If $R_1$ in formula V or Va is acetyl, the 0-acetyl group is split off simultaneously with the reduction of the carbonyl groups, and in this case a compound of the formula I is obtained, wherein $R_1$ is hydrogen. The reaction product is isolated and crystallized by conventional methods.

Method D

For the preparation of a compound of the formula I wherein $R_1$ is methyl or acetyl, by methylating or acetylating, respectively, a compound of the formula I wherein $R_1$ is hydrogen.

The methylation is effected in conventional manner, that is, by reacting the starting compound with a conventional methylating agent, such as diazomethane, a methyl ester of an inorganic acid, preferably dimethylsulfate, or a phenyl trimethylammonium compound.

The acetylation is effected with conventional acetylating agents, such as an acetyl halide, preferably acetyl chloride, or acetic acid anhydride.

The methylation as well as the acetylation is advantageously carried out in the presence of an acidbinding agent, such as pyridine or another tertiary amine, and in the presence of an inert solvent medium, preferably methylene chloride.

The starting compounds required for methods A to D are, to a large extent, known compounds or may be prepared by known methods.

For instance, a compound of the formula II may be obtained by reacting a corresponding N-methyl derivative with cyanogen bromide to form the analogous N-cyano-northebaine which is then hydrolized under alkaline conditions; depending upon the hydrolysis conditions, the nor-compound of the formula II wherein $R_1$ is either methyl or hydrogen is obtained, that is, alkaline hydrolysis under more severe conditions simultaneously splits off the 0-methyl group.

A compound of the formula VI may be obtained by reacting a compound of the formula II with an acyl halide of the formula

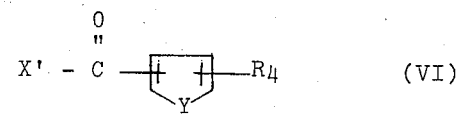 (VI)

wherein $R_4$ and Y have the meanings previously defined and X' is halogen, preferably chlorine. Likewise, a compound of the formula Va may be obtained by reacting a Diels-Alder adduct of a nor-compound of the formula

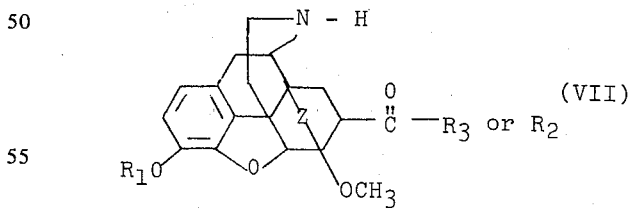 (VII)

wherein $R_1$, $R_2$, $R_3$ and Z have the meanings previously defined, with an acyl halide of the formula VII.

The 6,14 - endoetheno derivatives of compounds of the formulas II, V, Va and VII (where Z is —CH=CH—) may readily be converted into the corresponding saturated 6,14-endethano-derivatives (where Z is —$CH_2$—$CH_2$—) by catalytic hydrogenation.

The compounds embraced by formulas III, IV and VI are all known compounds, and many of them are readily available in commerce.

The compounds of the formula I are bases and therefore form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid, citric acid, malic acid, benzoic acid, phthalic acid, cinnamic acid, salicylic acid, ascorbic acid, 8-chlorotheophylline, methanesulfonic acid, ethanephosphonic acid or the like.

The following examples further illustrate the present invention and will enable others skilled in the art to understand it more completely. It should be understood, however, that the invention is not limited solely to the particular examples given below.

EXAMPLE 1

N-Furfuryl-6,14-endoetheno-7α-(1'-hydroxy-1'-methyl-ethyl)-tetrahydro-nororipavine and its hydrochloride by method A A mixture consisting of 3.69 gm (0.01 mol) of 6,14-endoetheno-7α-(1'-hydroxy-1'-methyl-ethyl)-tetrahydro-nororipavine, 1.26 gm (0.015 mol) of sodium bicarbonate, 1.28 gm (0.011 mol) of furfuryl chloride and 35 ml of a 2:1-mixture of tetrahydrofuran and dimethylformamide was refluxed for five hours, accompanied by stirring. Thereafter, the reaction solution was evaporated in vacuo, the residue was shaken with a mixture of methylene chloride and water, and the organic phase was separated, washed twice with water, dried over sodium sulfate and evaporated. The residue, the free base N-furfuryl-6,14-endoetheno-7α-(1'-hydroxy-1'-methyl-ethyl)-tetrahydro-nororipavine, was dissolved in 20 ml of absolute ethanol, the resulting solution was acidified with 2 ml of 5N hydrochloric acid, the acidic solution was carefully admixed with ether, and the precipitate formed thereby was collected. 2.4 gm (49.3% of theory) of the hydrochloride of the formula

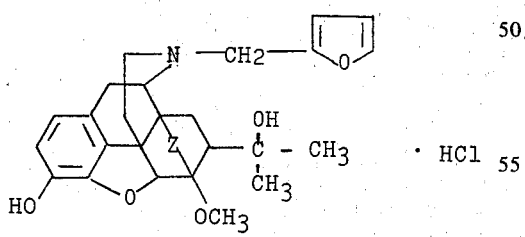

where Z is —CH=CH—, with a melting point of 224°–226°C. were obtained.

EXAMPLE 2

Using a procedure analogous to that described in Example 1, 46% of theory of N-furfuryl-6,14-endoetheno-7α-(hydroxy-methyl)-tetrahydro-northebaine, m. p. 113°–116°C., was obtained from 6,14-endetheno-7α-(hydroxy-methyl)-tetra-hydro-northebaine and furfuryl chloride.

EXAMPLE 3

Using a procedure analogous to that described in Example 1, N-furfuryl-6,14-endoetheno-7α-(hydroxy-methyl)-tetrahydro-nororipavine and 35% of theory of its hydrochloride, m. p. 212°–218°C., were obtained from 6,14-endoetheno-7α-(hydroxy-methyl)-tetrahydro-nororipavine and furfuryl chloride.

EXAMPLE 4

Using a procedure analogous to that described in Example 1, N-(3'-furylmethyl)-6,14-endoetheno-7α-(hydroxy-methyl)-tetrahydro-northebaine and 51% of theory of its hydrochloride, m. p. 254°–256°C., were obtained from 6,14-endoetheno-7α-(hydroxy-methyl)-tetrahydro-northebaine and 3-chloromethyl-furan.

EXAMPLE 5

Using a procedure analogous to that described in Example 1, N-(3'-furylmethyl)-6,14-endoetheno-7α-(hydroxy-methyl)-tetrahydro-nororipavine and 35% of theory of its hydrochloride, m. p. 222°–227°C., were obtained from 6,14-endoetheno-7α-(hydroxy-methyl)-tetrahydro-nororipavine and 3-chloromethyl-furan.

EXAMPLE 6

Using a procedure analogous to that described in Example 1, N-(2'-methyl-3'-furylmethyl)-6,14-endoetheno-7α-(hydroxy-methyl)-tetrahydro-northebaine and 46% of theory of its hydrochloride, m. p. 252°C.; were obtained from 6,14-endoetheno-7α-(hydroxy-methyl)-tetrahydro-northebaine and 2-methyl-3-chloromethyl-furan.

EXAMPLE 7

Using a procedure analogous to that described in Example 1, N-(2'-methyl-3'-furylmethyl)-6,14-endoetheno-7α-(hydroxy-methyl)-tetrahydro-nororipavine and 51% of theory of its hydrochloride, m. p. 220°–225°C., were obtained from 6,14-endoetheno-7α-(hydroxy-methyl)-tetrahydro-nororipavine and 2-methyl-3-chloromethyl-furan.

EXAMPLE 8

Using a procedure analogous to that described in Example 1, N-(3'-furylmethyl)-6,14-endoetheno-7α(-1''-hydroxyethyl)-tetrahydro-northebaine and 55% of theory of its hydrochloride, m. p. 237°–240°C., were obtained from 6,14-endoetheno-7α-(1'-hydroxyethyl)-tetrahydro-northebaine and 3-chloromethyl-furan.

EXAMPLE 9

Using a procedure analogous to that described in Example 1, N-(3'-furylmethyl)-6,14-endoetheno-7α-(1''-hydroxyethyl)-tetrahydro-nororipavine and 56.5% of theory of its hydrochloride, m. p. 250°–252°C., were obtained from 6,14-endoetheno-7α-(1'-hydroxyethyl)-tetrahydro-nororipavine and 3-chloromethyl-furan.

EXAMPLE 10

Using a procedure analogous to that described in Example 1, 45% of theory of N-furfuryl-6,14-endoetheno-7α-(1'-hydroxy-ethyl)-tetrahydro-northebaine, m. p. 112°–114°C., was obtained from 6,14-endoetheno-7α-(1′-hydroxy-methyl)-tetrahydro-northebaine and furfuryl chloride.

EXAMPLE 11

Using a procedure analogous to that described in Example 1, N-furfuryl-6,14-endoetheno-7α-(1′-hydroxy-ethyl)-tetrahydro-nororipavine and 59.6% of theory of its hydrochloride, m. p. 242°–244°C., were obtained from 6,14-endoetheno-7α-(1′-hydrocy-ethyl)-tetrahydro-nororipavine and furfuryl chloride.

EXAMPLE 12

Using a procedure analogous to that described in Example 1, N-(2′-methyl-3′-furylmethyl)-6,14-endoetheno-7α-(1″-hydroxy-ethyl)-tetrahydro-northebaine and 60% of theory of its hydrochloride, m. p. 170°C., were obtained from 6,14-endoetheno-7α-(1′-hydroxy-ethyl)-tetrahydro-northebaine and 2-methyl-3-chloromethyl-furan.

EXAMPLE 13

Using a procedure analogous to that described in Example 1, N-(2′-methyl-3′-furylmethyl)-6,14-endoetheno-7α-(1″-hydroxy-ethyl)-tetrahydro-nororipavine and 48% of theory of its hydrochloride, m. p. 180°C., were obtained from 6,14-endoethano-7α-(1′-hydroxy-ethyl)-tetrahydro-nororipavine and 2-methyl-3-chloromethyl-furan.

EXAMPLE 14

Using a procedure analogous to that described in Example 1, 52% of theory of N-(3′-furylmethyl)-6,14-endoethano-7α-(1″-hydroxy-ethyl)-tetrahydro-northebaine, m.p. 100°–102°C., of the formula

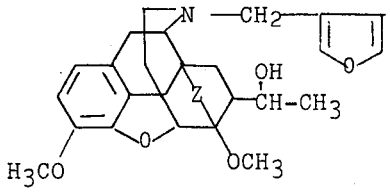

where Z is —CH$_2$—CH$_2$—, were obtained from 6,14-endoethano-7α-(1′-hydroxy-ethyl)-tetrahydro-northebaine and 3-chloromethyl-furan.

EXAMPLE 15

Using a procedure analogous to that described in Example 1, N-(3′-furylmethyl)-6,14-endoethano-7α-(1″-hydroxyethyl)-tetrahydro-nororipavine and 46% of theory of its hydrochloride, m.p. 198°C., were obtained from 6,14-endo-ethano-7α-(1′-hydroxy-ethyl)-tetrahydro-nororipavine and 3-chloromethyl-furan.

EXAMPLE 16

Using a procedure analogous to that described in Example 1, 67% of theory of N-furfuryl-6,14-endoethano-7α-(1′-hydroxy-ethyl)-tetrahydro-northebaine, m.p. 127°–128°C., were obtained from 6,14-endoethano-7α-(1′-hydroxy-ethyl)-tetrahydro-northebaine and furfuryl chloride.

EXAMPLE 17

Using a procedure analogous to that described in Example 1, N-furfuryl-6,14-endoethano-7α-(1′-hydroxy-ethyl)-tetrahydro-nororipavine and 48% of theory of its hydrochloride, m.p. 250°–252°C., were obtained from 6,14-endo-ethano-7α-(1′-hydroxy-ethyl)-tetrahydro-nororipavine and furfuryl chloride.

EXAMPLE 18

Using a procedure analogous to that described in Example 1, N-(2′-methyl-3′-furylmethyl)-6,14-endoethano-7α-(1″-hydroxy-ethyl)-tetrahydro-northebaine and 60% of theory of its hydrochloride, m.p. 175°C., were obtained from 6,14-endoethano-7α-(1′-hydroxy-ethyl)-tetrahydro-northebaine and 2-methyl-3-chloromethyl-furan.

EXAMPLE 19

Using a procedure analogous to that described in Example 1, N-(2′-methyl-3′-furylmethyl)-6,14-endoethano-7α-(1″-hydroxy-ethyl)-tetrahydro-nororipavine and 40% of theory of its hydrochloride, m.p. 250°–255°C., were obtained from 6,14-endoethano-7α-(1′-hydroxy-ethyl)-tetrahydro-nororipavine and 2-methyl-3-chloromethyl-furan.

EXAMPLE 20

Using a procedure analogous to that described in Example 1, 81.5% of theory of N-(3′-thienylmethyl)-6,14-endoetheno-7α-(α-hydroxy-benzyl)-tetrahydro-northebaine, m.p. 215°–216°C., of the formula

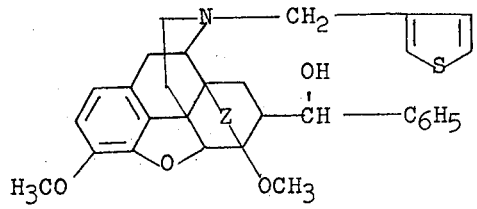

where Z is —CH=CH—, was obtained from 6,14-endo-etheno-7α-(α-hydroxy-benzyl)-tetrahydro-northebaine and 3-chloromethylthiopene.

EXAMPLE 21

Using a procedure analogous to that described in Example 1, 78% of theory of N-thenyl-6,14-endoetheno-7α-(α-hydroxy-benzyl)-tetrahydro-northebaine, m.p. 205°–207°C, was obtained from 6,14-endoetheno-7α-(α-hydroxy-benzyl)-tetrahydro-northebaine and thenyl chloride.

EXAMPLE 22

Using a procedure analogous to that described in Example 1, 87.5% of theory of N-furfuryl-6,14-endoetheno-7α-(α-hydroxy-benzyl)-tetrahydro-northebaine, m.p. 179°–180°C, was obtained from 6,14-endoetheno-7α-(α-hydroxy-benzyl)-tetrahydro-northebaine and furfuryl chloride.

EXAMPLE 23

Using a procedure analogous to that described in Example 1, N-(3′-furylmethyl)-6,14-endoetheno-7α-(1′-hydroxy-1″-methyl-ethyl)-tetrahydro-northebaine and 46% of theory of its hydrochloride, m.p. 208°–212°C, were obtained from 6,14-endoetheno-7α-(1′-hydroxy-1′-methyl-ethyl)-tetrahydro-northebaine and 3-chloromethyl-furan.

EXAMPLE 24

Using a procedure analogous to that described in Example 1, N-(3'-furylmethyl)-6,14-endoetheno-7α-(1''-hydroxy-1''-methyl-ethyl)-tetrahydro-nororipavine and 63% of theory of its hydrochloride, m.p. 215°–218°C, were obtained from 6,14-endoetheno-7α-(1'-hydroxy-1'-methyl-ethyl)-tetrahydro-nororipavine and 3-chloromethyl-furan.

EXAMPLE 25

Using a procedure analogous to that described in Example 1, 68% of theory of N-furfuryl-6,14-endoetheno-7α-(1'-hydroxy-1'-methyl-ethyl)-tetrahydro-northebaine, m.p. 108°–113°C, was obtained from 6,14-endoetheno-7α-(1'-hydroxy-1'-methyl-ethyl)-tetrahydro-northebaine and furfuryl chloride.

EXAMPLE 26

Using a procedure analogous to that described in Example 1, N-(2'-methyl-3'-furylmethyl)-6,14-endoetheno-7α-(1''-hydroxy-1''-methyl-ethyl)-tetrahydro-northebaine and 58% of theory of its hydrochloride, m.p. 190°–192°C, were obtained from 6,14-endoetheno-7α-(1'-hydroxy-1'-methyl-ethyl)-tetrahydro-northebaine and 2-methyl-3-chloromethyl-furan.

EXAMPLE 27

Using a procedure analogous to that described in Example 1, N-(2'-methyl-3'-furylmethyl)-6,14-endoetheno-7α-(1''-hydroxy-1''-methyl-ethyl)-tetrahydro-nororipavine and 72.5% of theory of its hydrochloride, m.p. 215°–218°C, were obtained from 6,14-endoetheno-7α-(1'-hydroxy-1'-methyl-ethyl) -tetrahydro-nororipavine and 2-methyl-3-chloromethyl-furan.

EXAMPLE 28

Using a procedure anlogous to that described in Example 1, N-(3'-thienylmethyl)-6,14-endoetheno-7α-(1''-hydroxy-1''-methyl-ethyl)-tetrahydro-northebaine and 64% of theory of its hydrochloride, m.p. 190°–193°C, were obtained from 6,14 -endoetheno-7α-(1'-hydroxy-1'-methyl-ethyl)-tetrahydro-northebaine and 3-chloromethyl-thiophene.

EXAMPLE 29

Using a procedure analogous to that described in Example 1, N-(3'-thienylmethyl)-6,14-endoetheno-7α-(1''-hydroxy-1''-methyl-ethyl)-tetrahydro-nororipavine and 75.8% of theory of its hydrochloride, m.p. 190°–194°C, were obtained from 6,14-endoetheno-7α-(1'-hydroxy-1'-methyl-ethyl)-tetra-hydro-nororipavine and 3-chloromethyl-thiophene.

EXAMPLE 30

Using a procedure analogous to that described in Example 1, N-thenyl-6,14-endoetheno-7α-(1'-hydroxy-1'-methylethyl)-tetrahydro-northebaine and 69.7% of theory of its hydrochloride, m.p. 182°–185°C, were obtained from 6,14-endo-etheno-7α-(1'-hydroxy-1'-methyl-ethyl)-tetrahydro-northebaine and thenyl chloride.

EXAMPLE 31

Using a procedure analogous to that described in Example 1, N-thienyl-6,14-endoetheno-7α-(1'-hydroxy-1'-methylethyl)-tetrahydro-nororipavine and 55.8% of theory of its hydrochloride, m.p. 216°–220°C, were obtained from 6,14-endo-entheno-7α-(1'-hydroxy-1'-methyl-ethyl)-tetrahydro-nororipavine and thenyl chloride.

EXAMPLE 32

Using a procedure analogous to that described in Example 1, N-(3'-furylmethyl)-6,14-endoethano-7α-(1''-hydroxy-1''-methyl-ethyl)-tetrahydro-northebaine and 46% of theory of its hydrochloride, m.p. 220°–223°C, were obtained from 6,14-endoethano-7α-(1'-hydroxy-1'-methyl-ethyl)-tetrahydro-northebaine and 3-chloromethyl-furan.

EXAMPLE 33

Using a procedure analogous to that described in Example 1, N-(3'-furylmethyl)-6,14-endoethano-7α-(1''-hydroxy-1''-methyl-ethyl)-tetrahydro-nororipavine and 60.2% of theory of its hydrochloride, m.p. 215°–220°C, were obtained from 6,14-endoethano-7α-(1'-hydroxy-1'-methyl-ethyl)-tetrahydro-noroipavine and 3-chloromethyl-furan.

EXAMPLE 34

Using a procedure analogous to that described in Example 1, 48.7% of theory of N-furfuryl-6,14-endoethano-7α-(1'-hydroxy-1'-methyl-ethyl)-tetrahydro-nothebaine, m.p. 130°–133°C, was obtained from 6,14-endoethano-7α-(1'-hydroxy-1'-methyl-ethyl)-tetrahydro-northebaine and furfuryl chloride.

EXAMPLE 35

Using a procedure analogous to that described in Example 1, N-furfuryl-6,14-endoethano-7α-(1'-hydroxy-1'-methyl-ethyl)-tetrahydro-nororipavine and 63.2% of theory of its hydrochloride, m.p. 215°–220°C, were obtained from 6,14-endo-ethano-7α-(1'-hydroxy-1'-methyl-ethyl)-tetrahydro-nororipavine and furfuryl chloride.

EXAMPLE 36

Using a procedure analogous to that described in Example 1, N-(2'-methyl-3'-furylmethyl)-6,14-endoethano-7α-(1''-hydroxy-1''-methyl-ethyl)-tetrahydro-northebaine and 73.4% of theory of its hydrochloride, m.p. 185°–187°C, were obtained from 6,14-endoethano-7α-(1'-hydroxy-1'-methyl-ethyl)-tetrahydro-northebaine and 2-methyl-3-chloromethyl-furan.

EXAMPLE 37

Using a procedure analogous to that described in Example 1, N-(2'-methyl-3'-furylmethyl)-6,14-endoethano-7α-(1''-hydroxy-1''-methyl-ethyl)-tetrahydro-nororipavine and 44% of theory of its hydrochloride, m.p. 218°–222°C, were obtained from 6,14-endoethano-7α-(1'-hydroxy-1'-methyl-ethyl)-tetrahydro-nororipavine and 2-methyl-3-chloromethyl-furan.

EXAMPLE 38

Using a procedure analogous to that described in Example 1, N-(3'-thienylmethyl)-6,14-endoethano-7α-(1''-hydroxy-1''-methyl-ethyl)-tetrahydro-northebaine and 65.7% of theory of its hydrochloride, m.p. 188°–191°C, were obtained from 6,14-endoethano-7α-(1'-hydroxy-1'-methyl-ethyl)-tetrahydronorthebaine and 3-chloromethyl-thiophene.

EXAMPLE 39

Using a procedure analogous to that described in Example 1, N-(3'-thienylmethyl)-6,14-endoethano-7α-(1''-hydroxy-1''-methyl-ethyl)-tetrahydro-nororipavine and 55.8% of theory of its hydrochloride, m.p. 245°–248°C, were obtained from 6,14-endoethano-7α-(1'-hydroxy-1'-methyl-ethyl)-tetrahydro-nororipavine and 3-chloromethyl-thiophene.

EXAMPLE 40

Using a procedure analogous to that described in Example 1, 62.2% of theory of N-thenyl-6,14-endothano-7α-(1'-hydroxy-1'-methyl-ethyl)-tetrahydro-northebaine, m.p. 145°–146°C, was obtained from 6,14-endoethano-7α-(1'-hydroxy-1'-methyl-ethyl)-tetrahydro-northebaine and thenyl chloride.

EXAMPLE 41

Using a procedure analogous to that described in Example 1, N-thenyl-6,14-endoethano-7α-(1'-hydroxy-1'-methyl-ethyl)-tetrahydro-nororipavine and 48% of theory of its hydrochloride, m.p. 222°–224°C, were obtained from 6,14-endo-ethano-7α-(1'-hydroxy-1'-methyl-ethyl)-tetrahydro-nororipavine and thenyl chloride.

EXAMPLE 42

Using a procedure analogous to that described in Example 1, N-(3'-furylmethyl)-6,14-endoethano-7α-(1''-hydroxy-1''-methyl-n-butyl)-tetrahydro-northebaine and 61% of theory of its hydrochloride, m.p. 190°–193°C, were obtained from 6,14-endoetheno-7α-(1'-hydroxy-1'-methyl-n-butyl)-tetrahydro-northebaine and 3-chloromethyl-furan.

EXAMPLE 43

Using a procedure analogous to that described in Example 1, N-(3'-furylmethyl)-6,14-endoetheno-7α-(1''-hydroxy-1''-methyl-n-butyl)-tetrahydro-noroipavine and 42% of theory of its hydrochloride, m.p. 200°–207°C, were obtained from 6,14-endoetheno-7α-(1'-hydroxy-1'-methyl-n-butyl)-tetrahydronororipavine and 3-chloromethyl-furan.

EXAMPLE 44

Using a procedure analogous to that described in Example 1, N-furfuryl-6,14-endoetheno-7α-(1'-hydroxy-1'-methyl-n-butyl)-tetrahydro-northebaine and 75.8% of theory of its hydrochloride, m.p. 160°–165°C, were obtained from 6,14-endo-etheno-7α-(1'-hydroxy-1'-methyl-n-butyl)-tetrahydro-northebaine and furfuryl chloride.

EXAMPLE 45

Using a procedure analogous to that described in Example 1, N-furfuryl-6,14-endoetheno-7α-(1'-hydroxy-1'-methyl-n-butyl)-tetrahydro-nororipavine and 54.5% of theory of its hydrochloride, m.p. 185°–187°C, were obtained from 6,14-endoetheno-7α-(1'-hydroxy-1'-methyl-n-butyl)-tetrahydro-nororipavine and furfuryl chloride.

EXAMPLE 46

Using a procedure analogous to that described in Example 1, N-(2'-methyl-3'-furylmethyl)-6,14-endoetheno-7α-(1''-hydroxy-1''-methyl-n-butyl)-tetrahydro-northebaine and 49.4% of theory of its hydrochloride, m.p. 196°–198°C, were obtained from 6,14-endoetheno-7α-(1'-hydroxy-1'-methyl-n-butyl)-tetrahydro-northebaine and 2-methyl-3-chloromethyl-furan.

EXAMPLE 47

Using a procedure analogous to that described in Example 1, 47.5% of theory of N-(2'-methyl-3'-furylmethyl)-6,14-endoetheno-7α-(1''-hydroxy-1''-methyl-n-butyl)-tetrahydro-nororipavine, m.p. 220°–222°C, was obtained from 6,14-endoetheno-7α-(1'-hydroxy-1'-methyl-n-butyl)-tetrahydro-nororipavine and 2-methyl-3-chloromethyl-furan.

EXAMPLE 48

Using a procedure analogous to that described in Example 1, 59.8% of theory of N-(3'-thienylmethyl)-6,14-endoenthano-7α-(1''-hydroxy-1''-methyl-n-butyl)-tetrahydro-northebaine, m.p. 172°–173°C, was obtained from 6,14-endoetheno-7α-(1'-hydroxy-1'-methyl-n-butyl)-tetrahydro-northebaine and 3-chloromethyl-thiophene.

EXAMPLE 49

Using a procedure analogous to that described in Example 1, 43.8% of theory of N-thenyl-6,14-endoetheno-7α-(1'-hydroxy-1'-methyl-n-butyl)-tetrahydro-northebaine, m.p. 132°–133°C, was obtained from 6,14-endoetheno-7α-(1'-hydroxy-1'-methyl-n-butyl)-tetrahydro-northebaine and thenyl chloride.

EXAMPLE 50

Using a procedure analogous to that described in Example 1, N-furfuryl-6,14-endoethano-7α-(1'-hydroxy-1'-methyl-n-butyl)-tetrahydro-northebaine and 42.8% of theory of its hydrochloride, m.p. 154°–156°C, were obtained from 6,14-endoethano-7α-(1'-hydroxy-1'-methyl-n-butyl)-tetrahydro-northebaine and furfuryl chloride.

EXAMPLE 51

Using a procedure analogous to that described in Example 1, N-(3'-furylmethyl)-6,14-endoethano-7α-(1''-hydroxy-1''-methyl-n-butyl)-tetrahydro-northebaine and 74% of theory of its hydrochloride, m.p. 218°C, were obtained from 6,14-endoethano-7α-(1'-hydroxy-1'-methyl-n-butyl)-tetrahydro-northebaine and 3-chloromethyl-furan.

EXAMPLE 52

Using a procedure analogous to that described in Example 1, N-(2'-methyl-3'-furylmethyl)-6,14-endoethano-7α-(1''-hydroxy-1''-methyl-n-butyl)-tetrahydro-northebaine and 75.8% of theory of its hydrochloride, m.p. 172°–174°C, were obtained from 6,14-endoethano-7α-(1'-hydroxy-1'-methyl-n-butyl)-tetrahydro-northebaine and 2-methyl-3- chloromethyl-furan.

EXAMPLE 53

Using a procedure analogous to that described in Example 1, 66.7% of theory of N-(3'-furylmethyl)-6,14-endoetheno-7α-(1''-hydroxy-1''-methyl-3''-phenyl-n-propyl)-tetra-hydro-northebaine, m.p. 170°–171°C, was obtained from 6,14-endoetheno-7α-(1'-hydroxy-1'-methyl-3'-phenyl-n-propyl)-tetrahydro-northebaine and 3-chloromethyl-furan.

EXAMPLE 54

Using a procedure analogous to that described in Example 1, 52% of theory of N-(3'-furylmethyl)-6,14-etheno-7α-(1''-hydroxy-1''-methyl-3''-phenyl-n-propyl)-tetra-hydro-nororipavine, m.p. 245°–247°C, was obtained from 6-14-endoetheno-7α-(1'-hydroxy-1'-methyl-3'-phenyl-n-propyl)-tetrahydro-nororipavine and 3-chloromethyl-furan.

EXAMPLE 55

Using a procedure analogous to that described in Example 1, N-furfuryl-6,14-endoetheno-7α-(1'-hydroxy-1'-methyl-3'-phenyl-n-propyl)-tetrahydro-northbaine and 47.7% of theory of its hydrochloride, m.p. 169°–171°C, were obtained from 6,14-endoetheno-7α-(1'-hydroxy-1'-methyl-3'-phenyl-n-propyl)-tetrahydro-northbaine and furfuryl chloride.

EXAMPLE 56

Using a procedure analogous to that described in Example 1, 74% of theory of N-furfuryl-6,14-endoetheno-7α(1'-hydroxy-1'-methyl-3'-phenyl-n-propyl)-tetrahydro-nororipavine, m.p. 222°–224°C, was obtained from 6,14-endoetheno-7α-(1'-hydroxy-1'-methyl-3'-phenyl-n-propyl)-tetrahydro-nororipavine and furfuryl chloride.

EXAMPLE 57

Using a procedure analogous to that described in Example 1, N-(2'-methyl-3'-furylmethyl)-6,14-endoetheno-7α-(1''-hydroxy-1''-methyl-3''-phenyl-n-propyl)-tetrahydro-northebaine and 56.7% of theory of its hydrochloride, m.p. 165°–169°C, were obtained from 6,14-endoetheno-7α-(1'-hydroxy-1'-methyl-3'-phenyl-n-propyl)-tetrahydro-northebaine and 2-methyl-3-chloromethyl-furan.

EXAMPLE 58

Using a procedure analogous to that described in Example 1, N-(2'-methyl-3'-furylmethyl)-6,14-endoetheno-7α-(1''-hydroxy-1''-methyl-3''-phenyl-n-propyl)-tetrahydro-nororipavine and 40% of theory of its hydrochloride, m.p. 232°–234°C, were obtained from 6,14-endoetheno-7α-(1'-hydroxy-1'-methyl-3'-phenyl-n-propyl)-tetrahydro-nororipavine and 2-methyl-3-chloromethyl-furan.

EXAMPLE 59

Using a procedure analogous to that described in Example 1, 84.5% of theory of N-(3'-thienylmethyl)-6,14-2ndoetheno-7α-(1'''-hydroxy-1'''-methyl-3''-phenyl-n-propyl)-tetra-hydro-northbaine, m.p. 117°–119°C, was obtained from 6,14-endoetheno-7α-(1'-hydroxy-1'-methyl-3'-phenyl-n-propyl)-tetrahydro-northebaine and 3-chloromethyl-thiophene.

EXAMPLE 60

Using a procedure analogous to that described in Example 1, 77.5% of theory of N-thenyl-6,14-endoetheno-7α-(1'-hydroxy-1'-methyl-3'-phenyl-n-propyl)-tetrahydro-northbaine, m.p. 139°–140°C, was obtained from 6,14-endoetheno-7α-(1'-hydroxy-1'-methyl-3'-phenyl-n-propyl)-tetrahydro-northbaine and thenyl chloride.

EXAMPLE 61

N-(5'-Methyl-furfuryl)-6,14-endoetheno-7α-(1''-hydroxy-1''-methyl-ethyl)-tetrahydro-nororipavine and its hydrochloride by method B 3.69 gm (0.01 mol) of 6,14-endoetheno-7α-(1'-hydroxy-1'-methyl-ethyl)-tetrahydro-nororipavine were dissolved in 10 ml of aqueous 50% acetic acid, and, while stirring the resulting solution, it was admixed with 1.0 gm of aqueous 30% formaldehyde (0.01 mol formaldehyde). Subsequently, while stirring, 0.82 gm (0.01 mol) of 2-methyl-furan was slowly added dropwise to the mixture, and the resulting mixture was then stirred for 15 hours at room temperature. Thereafter, the reaction mixture was made alkaline with concentrated ammonia while adding ice, then it was extracted with methylene chloride, and the organic phase was washed several times with water, dried over sodium sulfate and evaporated. The residue, the free base N-(5'-methyl-furfuryl)-6,14-endoetheno-7α-(1''-hydroxy-1''-methyl-ethyl)-tetrahydronororipavine, was dissolved in ethanol, the solution was acidified with ethanolic hydrochloric acid, and ether was added until the solution began to turn cloudy. The precipitate formed thereby was collected, yielding 3.2 gm (62% of theory) of the hydrochloride which had a melting point of 191°–195°C.

EXAMPLE 62

N-(3'-Methyl-furfuryl)-6,14-endoetheno-7α-(1''-hydroxy-1''-methyl-ethyl)-tetrahydro-nororipavine and its hydrochloride by method C 3.69 gm (0.01 mol) of 6,14-endoetheno-7α-(1'-hydroxy-1'-methyl-ethyl)-tetrahydro-nororipavine were suspended in 35 ml of methanol, the suspension was admixed with a solution of 2.5 gm of potassium carbonate in 4 ml of water, and then, while cooling the mixture, 1.74 gm (0.011 mol) of 3-methyl-furan-2-carboxylic acid chloride were added dropwise over a period of 20 minutes, and the resulting mixture was stirred for three hours. Thereafter, the reaction mixture was evaporated in vacuo, the residue was dissolved in methylene chloride, and the resulting solution was washed successively several times with water, dilute hydrochloric acid, dilute sodium bicarbonate solution and again with water. The organic phase was dried over sodium sulfate, evaporated in vacuo, the residue was dissolved in 50 ml of absolute tetrahydrofuran, the resulting solution was added dropwise to a solution of 0.76 gm (0.02 mol) of lithium aluminum hydride in 25 ml of tetrahydrofuran at 5° to 10°C, and the mixture was stirred overnight at room temperature. Thereafter, the resulting suspension was carefully admixed with 1.5 ml of water while cooling on ice, then 75 ml of saturated aqueous diammonium tartrate were added, and the mixture was allowed to stand for one hour. The tetrahydrofuran (upper) phase was separated and evaporated, the aqueous phase was extracted twice with methylene chloride, the residue of the tetrahydrofuran phase evaporation was dissolved and the combined methylene chloride extracts, and the resulting solution was washed several times with water, dried over sodium sulfate and evaporated in vacuo. The residue, the free base N-(3'-methyl-furfuryl)-6,14-endoetheno-7α-(1''-hydroxy-1''-methyl-ethyl)-tetrahydro-nororipavine, was dissolved in ethanol, the solution was acidified with ethereal hydrochloric acid, and the crystalline substance which separated out was collected, yielding 2.2 gm (45% of theory) of the hydrochloride which had a melting point of 195°C.

EXAMPLE 63

Using a procedure analogous to that described in Example 62, N-(3'-methyl-furfuryl)-6,14-endoetheno-7α-(1''-hydroxy-ethyl)-tetrahydro-northebaine and 60.4% of theory of its hydrochloride, m.p. 165°–169°C, were obtained from 6,14-endoetheno-7α-(1'-hydroxy-ethyl)-tetrahydro-northebained and 3-methyl-furoyl chloride, and subsequent reduction of the intermediate with lithium aluminum hydride.

EXAMPLE 64

Using a procedure analogous to that described in Example 62, N-(3'-methyl-furfuryl)-6,14-endoetheno-7α-(1''-hydroxy-ethyl)-tetrahydro-nororipavine and 77.6% of theory of its hydrochloride, m.p. 230°–232°C, were obtained from 6,14-endoetheno-7α-(1'-hydroxy-ethyl)-tetrahydro-nororipavine and 3-methyl-furoyl chloride, and subsequent reduction of the intermediate with lithium aluminum hydride.

EXAMPLE 65

Using a procedure analogous to that described in Example 62, N-(3'-methyl-furfuryl)-6,14-endoethano-7α-(1''-hydroxy-ethyl)-tetrahydro-northebaine and 64.4% of theory of its hydrochloride, m.p. 190°–192°C, were obtained from 6,14-endoethano-7α-(1'-hydroxy-ethyl)-tetrahydro-northebaine and 3-methyl-furoyl chloride, and subsequent reduction of the intermediate with lithium aluminum hydride.

EXAMPLE 66

Using a procedure analogous to that described in Example 62, N-(3'-methyl-furfuryl)-6,14-endoethano-7α-(1''-hydroxy-ethyl)-tetrahydro-nororipavine and 47.6% of theory of its hydrochloride, m.p. 230°–235°C, were obtained from 6,14-endoethano-7α-(1'-hydroxy-ethyl)-tetrahydro-nororipavine and 3-methyl-furoyl chloride, and subsequent reduction of the intermediate with lithium aluminum hydride.

EXAMPLE 67

Using a procedure analogous to that described in Example 62, N-(3'-methyl-furfuryl)-6,14-endoetheno-7α-(1''-hydroxy-1''-methyl-ethyl)-tetrahydro-northebaine and 62.3% of theory of its hydrochloride, m.p. 170°–172°C, were obtained from 6,14-endoetheno-7α-(1'-hydroxy-1'-methyl-ethyl)-tetra-hydro-northebaine and 3-methyl-furoyl chloride, and subsequent reduction of the intermediate with lithium aluminum hydride.

EXAMPLE 68

Using a procedure analogous to that described in Example 62, N-(3'-methyl-furfuryl)-6,14-endoethano-7α-(1''-hydroxy-1''-methyl-ethyl)-tetrahydro-northebaine and 58% of theory of its hydrochloride, m.p. 155°–157°C, were obtained from 6,14-endoethano-7α-(1'-hydroxy-1'-methyl-ethyl)-tetra-hydro-northebaine and 3-methyl-furoyl chloride, and subsequent reduction of the intermediate with lithium aluminum hydride.

EXAMPLE 69

Using a procedure analogous to that described in Example 62, N-(3'-methyl-furfuryl)-6,14-endoethano-7α-(1''-hydroxy-1''-methyl-ethyl)-tetrahydro-nororipavine and 72.5% of theory of its hydrochloride, m.p. 210°–212°C, were obtained from 6,14-endoethano-7α-(1'-hydroxy-1'-methyl-ethyl))-tetra-hydro-nororipavine and 3-methyl-furoyl chloride, and subsequent reduction of the intermediate with lithium aluminum hydride.

EXAMPLE 70

Using a procedure analogous to that described in Example 62, N-(3'-methyl-furfuryl)-6,14-endoetheno-7α-(1''-hydroxy-1''-methyl-n-butyl)-tetrahydro-northebaine and 71.2% of theory of its hydrochloride, m.p. 170°–172°C, , were obtained from 6,14-endoetheno-7α-(1'-hydroxy-1'-methyl-n-butyl)-tetra-hydro-northebaine and 3-methyl-furoyl chloride, and subsequent reduction of the intermediate with lithium aluminum hydride.

EXAMPLE 71

Using a procedure analogous to that described in Example 62, 50.4% of theory of N-(3'-methyl-furfuryl)-6,14-endoetheno-7α-(1''-hydroxy-1''-methyl-n-butyl)-tetrahydro-noroipavine, m.p. 204°–206°C, was obtained from 6,14-endoetheno-7α-(1'-hydroxy-1'-methyl-n-butyl)-tetrahydro-nororipavine and 3-methyl-furoyl chloride, and subsequent reduction of the intermediate with lithium aluminum hydride.

EXAMPLE 72

Using a procedure analogous to that described in Example 62, N-(3'-methyl-furfuryl)-6,14-endoethano-7α-(1''-hydroxy-1''-methyl-n-butyl)-tetrahydro-northebaine and 56.8% of theory of its hydrochloride, m.p. 155°–159°C, were obtained from 6,14-endoethano-7α-(1'-hydroxy-1'-methyl-n-butyl)-tetrahydro-northebaine and 3-methyl-furoyl chloride, and subsequent reduction of the intermediate with lithium aluminum hydride.

EXAMPLE 73

Using a procedure analogous to that described in Example 62, N-(3'-methyl-furfuryl)-6,14-endoetheno-7α-(1''-hydroxy-1''-methyl-3''-phenyl-n-propyl)-tetrahydro-northebaine and 56.7% of theory of its hydrochloride, m.p. 211°C, were obtained from 6,14-endoetheno-7α-(1'-hydroxy-1'-methyl-3'-phenyl-n-propyl)-tetrahydro-northebaine and 3-methyl-furoyl chloride, and subsequent reduction of the intermediate with lithium aluminum hydride.

EXAMPLE 74

Using a procedure analogous to that described in Example 62, N-(3'-methyl-furfuryl)-6,14-endoetheno-7α-(1''-hydroxy-1''-methyl-3''-phenyl-n-propyl)-tetrahydro-nororipavine and 61% of theory of its hydrochloride, m.p. 247°–248°C, were obtained from 6,14-endoetheno-7α-(1'-hydroxy-1'-methyl-3'-phenyl-n-propyl)-tetrahydro-nororipavine and 3-methyl-furoyl chloride, and subsequent reduction of the intermediate with lithium aluminum hydride.

EXAMPLE 75

Using a procedure analogous to that described in Example 62, N-(3'-methyl-furfuryl)-6,14-endoetheno-7α-(1''-hydroxy-methyl)-tetrahydro-northebaine and 33% of theory of its hydrochloride, m.p. 200°–202°C, were obtained from 6,14-endoetheno-7α-(1'-hydroxy-methyl)-tetrahydro-northebaine and 3-methyl-furoyl chloride, and subsequent reduction of the intermediate with lithium aluminum hydride.

EXAMPLE 76

Using a procedure analogous to that described in Example 62, N-(3'-methyl-furfuryl)-6,14-endoetheno-7α-(1''-hydroxy-methyl)-tetrahydro-nororipavine and 34% of theory of its hydrochloride, m.p. 195°–199°C, were obtained from 6,14-endoetheno-7α-(1'-hydroxy-methyl)-tetrahydro-nororipavine and 3-methyl -furoyl chloride, and subsequent reduction of the intermediate with lithium aluminum hydride.

EXAMPLE 77

N-furfuryl-3-(O-acetyl)1-(O-acetyl)-6,14-endoetheno-7α-(1'-hydroxy-1'-methyl esthyl)-tetrahydro-nororipavine by method D A mixture consisting of 4.46 gm (0.01 mol) of N-furfuryl-6,14-endoetheno-7α-(1'-hydroxy-1'-methyl-ethyl)-tetrahydro-nororipavine, 10 ml of acetic acid anhydride and 0.82 gm (0.1 mol) of sodium acetate was heated for one hour at 100°C. Thereafter, the reaction mixture was allowed to cool, was then poured over 100 gm of ice, and after an interval of five minutes the aqueous mixture was made distinctly alkaline with aqueous 30% sodium hydroxide. The resulting suspension was extracted with methylene chloride, and the organic extract solution was washed several times with water, dried over sodium sulfate and evaporated, yielding 3 gm (62.5% of theory) of the compound of the formula

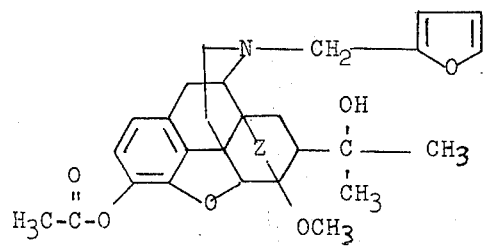

where Z is —CH=CH—, which had a melting point of 122°–123°C (recrystallized from petroleum ether).

The compounds of the present invention, that is, those embraced by formula I and their non-toxic, pharmacologically acceptable acid addition salts, have useful pharmacodynamic properties. More particularly, the compounds of the instant invention exhibit non-narcotic analgesic and antitussive activities in warm-blooded animals such as mice and rats.

All of the compounds of the present invention proved to be ineffective as analgesics in the Haffner test for analgesia [Deutsche Medizinische Wochenschrift 55, 731 (1929)] on mice and rats.

On the other hand, the compounds of this invention exhibit a distinct, dose-dependent analgesic activity in more sensitive phamacological tests for analgesia, such as the hot-plate test [J. Pharmacol. Exp. Therap. 80, 300 (1944)] or the writhing test [J. Pharmacol. Exp. Therap. 154, 319 (1966)].

In accordance with presently prevailing teachings [Adv. Chem. Soc. 49, 162-169 (1964)], inactivity in the Haffner test is indicative of non-narcotic properties, while activity in the hot-plate test and/or writhing test proves analgesic properties.

For pharmaceutical purposes the compounds according to the present invention are administered to warm-blooded animals perorally, enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral analgesic and antitussive dosage unit of the compounds according to the present invention is from 0.016 to 6.7 mgm/kg body weight, preferably 0.41 to 3.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 78

Tablets

The tablet composition is compounded from the following ingredients:

| | | |
|---|---:|---|
| N-Furfuryl-7α-(hydroxy-methyl)-6,14-endoetheno-tetrahydro-northebaine | 50.0 | parts |
| Lactose | 95.0 | '' |
| Corn starch | 45.0 | '' |
| Colloidal silicic acid | 2.0 | '' |
| Soluble starch | 5.0 | '' |
| Magnesium stearate | 3.0 | '' |
| Total | 200.0 | parts |

Preparation

The northebaine compound is intimately admixed with the lactose and the corn starch, the mixture is moistened with an aqueous 10% solution of the soluble starch, the moist mass is forced through a 1 mm-mesh screen, the resulting granulate is dried at 40°C, the dry granulate is admixed with the colloidal silicic acid, and the composition is compressed into 200 mgm-tablets in a conventional tablet making machine. Each tablet contains 50 mgm of the northebaine compounds and is an oral dosage unit composition with effective analgesic and antitussive actions.

EXAMPLE 79

Coated pills

The pill core composition is compounded from the following ingredients:

| | | |
|---|---:|---|
| N-Furfuryl-6,14-endoetheno-7α-(hydroxy-methyl)-tetrahydro-nororipavine hydrochloride | 75.0 | parts |
| Lactose | 100.0 | '' |
| Corn starch | 65.0 | '' |
| Colloidal silicic acid | 2.0 | '' |
| Soluble starch | 5.0 | '' |
| Magnesium stearate | 3.0 | '' |
| Total | 250.0 | parts |

Preparation

The ingredients are compounded in the same manner as in Example 78, and the composition is compressed into 250 mgm-pill cores which are subsequently coated with a thin shell consisting essentially of a mixture of sugar, talcum and gum arabic and finally polished with beeswax. Each coated pill contains 75 mgm of the nororipavine compound and is an oral dosage unit composition with effective analgesic and antitussive activities.

EXAMPLE 80

Suppositories

The suppository composition is compounded from the following ingredients:

| | | |
|---|---:|---|
| N-Furfuryl-6,14-endoetheno-7α-(1'-hydroxy-1'-methyl-ethyl)-tetrahydro-nororipavine hydrochloride | 50.0 | parts |
| Lactose | 250.0 | '' |
| Suppository base (e.g. cocoa butter) | 1400.0 | '' |
| Total | 1700.0 | parts |

Preparation

The nororipavine compound is intimately admixed with the lactose, and the mixture is blended with the aid of an immersion homogenizer into the suppository base which had previously been melted and cooled to about 40°C. 1700 mgm-portions of the composition are poured into cooled suppository molds and allowed to harden therein. Each suppository contains 50 mgm of the nororipavine compound and is a rectal dosage unit composition with effective analgesic and antitussive actions.

EXAMPLE 81

Hypodermic solution

The solution is compounded from the following ingredients:

| | | | |
|---|---|---:|---|
| N-(2'-Methyl-3'-furylmethyl)-6,14-endoetheno-7α-(hydroxy-methyl)-tetrahydro-nororipavine | | 75.0 | parts |
| Socium chloride | | 5.0 | '' |
| Double-distilled water | q.s.ad | 2000.0 | '' |
| | | | by vol. |

Preparation

The nororipavine compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 75 mgm of the nororipavine compound, and its contents are an injectable dosage unit composition with effective analgesic and antitussive actions.

EXAMPLE 82

Drop solution

The solution is compounded from the following ingredients:

| | | | |
|---|---|---:|---|
| N-Furfuryl-6,14-endoetheno-7α-(1'-hydroxy-1'-methyl-ethyl)-tetrahydro-nororipavine hydrochloride | | 0.80 | parts |
| Methyl p-hydroxy-benzoate | | 0.06 | '' |
| Propyl p-hydroxy-benzoate | | 0.04 | '' |
| Demineralized water | q.s.ad | 00.0 | |
| | | | by vol. |

Preparation

The nororipavine compound and the p-hydroxy-benzoates are dissolved in the demineralized water, the solution is filtered, and the filtrate is filled into 100 ml-bottles. 10 ml of the solution contain 80 mgm of the nororipavine compound and are an oral dosage unit composition with effective analgesic and antitussive actions.

Analogous results are obtained when any one of the other compounds embraced by formula I or a non-toxic acid addition salt thereof is substituted for the particular northebaine compound in Examples 78 through 82. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

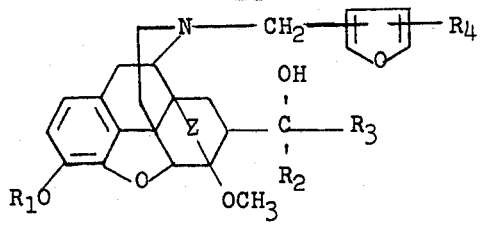

wherein
R₁ is hydrogen, methyl or acetyl,
R₂ is hydrogen or methyl,
R₃ is hydrogen, methyl, n-propyl, phenethyl or phenyl,
R₄ is hydrogen or methyl, and
Z is —CH=CH— or —CH₂—CH₂—, or a non-toxic, pharmacologically acceptable acid addition salt thereof.

2. A compound of claim 1, which is of the formula

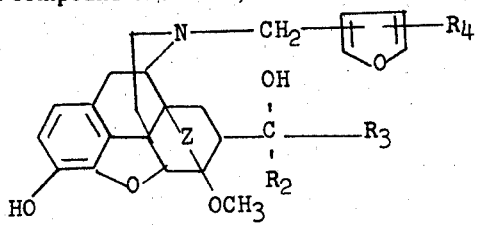

wherein
R₂ is hydrogen or methyl,
R₃ is hydrogen, methyl, n-propyl, phenethyl or phenyl,
R₄ is hydrogen or methyl, and
Z is —CH=CH— or —CH₂—CH₂—
or a non-toxic, pharmacologically acceptable acid addition salt thereof.

3. A compound of claim 1, which is N-furfuryl-6,14-endoetheno-7α-(hydroxy-methyl)-tetrahydro-northebaine or a non-toxic, pharmacologically acceptable acid addition salt thereof.

4. A compound of claim 1, which is N-furfuryl-6,14-endoetheno-7α-(hydroxy-methyl)-tetrahydro-nororipavine or a non-toxic, pharmacologically acceptable acid addition salt thereof.

5. A compound of claim 1, which is N-furfuryl-6,14-endoetheno-7α-(1'-hydroxy-1'-methyl-ethyl)-tetrahydronororipavine or a non-toxic, pharmacologically acceptable acid addition salt thereof.

6. A compound of claim 1, which is N-(2'-methyl-3'-furylmethyl)-6,14-endoetheno-7α-(hydroxy-methyl)-tetra-hydro-nororipavine or a non-toxic, pharmacologically acceptable acid addition salt thereof.

* * * * *

UNITED STATES PATENT OFFICE
CERTIFICATE OF CORRECTION

Patent No. 3,931,189     Dated January 6, 1976

Inventor(s) ADOLF LANGBEIN, HERBERT MERZ, GERHARD WALTHER and KLAUS STOCKHAUS

It is certified that error appears in the above-identified patent and that said Letters Patent are hereby corrected as shown below:

[75] Inventor "Kalus Stockhaus" should read -- Klaus Stockhaus --

In Col. 4, Line 63   after "-CH=" -- ∧ -- should be deleted

In Col. 6, Line 66   "ir" should read -- in --

In Col. 7, Line 10   "-hydrocy-" should read -- -hydroxy- --

In Col. 10, Line 21   "noroipavine" should read -- nororipavine --

In Col. 10, Line 28   "nothebaine" should read -- northebaine --

In Col. 11, Line 40   "noroipa-" should read -- nororipa- --

In Col. 12, Line 21   "enthano-" should read -- etheno- --

In Col. 13, Line 16   "endo" should be inserted before -- etheno --

In Col. 13, Line 28   "47.7%" should read -- 57.7% --

In Col. 13, Line 31   "northbaine" should read -- northebaine --

In Col. 14, Line 14   "northbaine" should read -- northebaine --

In Col. 16, Line 62   "noroipavine" should read -- nororipavine --

In Col. 17, Line 62   "1-(o-acetyl)" should be deleted

Signed and Sealed this twentieth Day of April 1976

[SEAL]

Attest:

RUTH C. MASON          C. MARSHALL DANN
*Attesting Officer*          *Commissioner of Patents and Trademarks*